US012661023B2

(12) United States Patent
Wang

(10) Patent No.: US 12,661,023 B2
(45) Date of Patent: Jun. 23, 2026

(54) STATE INFORMATION DETERMINATION METHOD AND DEVICE, CONTROL METHOD AND DEVICE

(71) Applicant: Li Wang, Shanghai (CN)

(72) Inventor: Li Wang, Shanghai (CN)

( * ) Notice: Subject to any disclaimer, the term of this patent is extended or adjusted under 35 U.S.C. 154(b) by 363 days.

(21) Appl. No.: 18/344,713

(22) Filed: Jun. 29, 2023

(65) Prior Publication Data

US 2023/0337924 A1 Oct. 26, 2023

Related U.S. Application Data

(63) Continuation of application No. PCT/CN2021/141715, filed on Dec. 27, 2021.

(30) Foreign Application Priority Data

Dec. 30, 2020 (CN) .......................... 202011624641.6

(51) Int. Cl.
*A61B 5/024* (2006.01)
(52) U.S. Cl.
CPC ................................ *A61B 5/02405* (2013.01)
(58) Field of Classification Search
None
See application file for complete search history.

(56) References Cited

U.S. PATENT DOCUMENTS

2005/0267362 A1* 12/2005 Mietus ................. A61B 5/0816
600/483
2007/0100246 A1* 5/2007 Hyde ................. A61B 5/02405
600/509

(Continued)

FOREIGN PATENT DOCUMENTS

CN 103717125 A 4/2014
CN 107847156 A 3/2018

(Continued)

OTHER PUBLICATIONS

First Office Action issued in counterpart Chinese Patent Application No. 202011624641.6, dated Sep. 30, 2024.

(Continued)

*Primary Examiner* — Ankit D Tejani
(74) *Attorney, Agent, or Firm* — Westbridge IP LLC

(57) ABSTRACT

Disclosed are a state information determination method and device, and a control method and device, which relate to the field of medical data processing technologies. The state information determination method includes: determining, based on a preset analysis time interval, a state evaluation parameter corresponding to a subject to be tested; and determining, based on the state evaluation parameter, first state information corresponding to the subject to be tested. The state evaluation parameter includes at least one of a first heart-rate characterization parameter, a first heart-rate variability characterization parameter, a second heart-rate characterization parameter, and a second heart-rate variability characterization parameter. The first heart-rate characterization parameter and the first heart-rate variability characterization parameter correspond to a first time interval, and the second heart-rate characterization parameter and the second heart-rate variability characterization parameter correspond to a second time interval. Accuracy and comparability at different times of determined first state information are improved.

19 Claims, 8 Drawing Sheets

(56)  References Cited

U.S. PATENT DOCUMENTS

| | | |
|---|---|---|
| 2007/0260147 A1 | 11/2007 | Giftakis et al. |
| 2016/0256060 A1 | 9/2016 | Katra |
| 2018/0035899 A1 | 2/2018 | Gunderson et al. |
| 2019/0290147 A1 | 9/2019 | Persen et al. |
| 2020/0214644 A1 | 7/2020 | Moon |
| 2020/0297955 A1 | 9/2020 | Shouldice et al. |
| 2020/0335211 A1 | 10/2020 | Gopalakrishnan |

FOREIGN PATENT DOCUMENTS

| | | |
|---|---|---|
| CN | 108135534 A | 6/2018 |
| CN | 109157191 A | 1/2019 |
| CN | 109875528 A | 6/2019 |
| CN | 112004462 A | 11/2020 |
| JP | 2012183177 A | 9/2012 |
| JP | 2018023676 A | 2/2018 |
| JP | 2019107513 A | 7/2019 |
| KR | 1020130134052 A | 12/2013 |
| RU | 2257842 C2 | 8/2005 |
| WO | 2019246234 A1 | 12/2019 |

OTHER PUBLICATIONS

Second Office Action issued in counterpart Chinese Patent Application No. 202011624641.6, dated May 28, 2025.

Adamopoulos et al., Comparison of Different Methods for Assessing Sympathovagal Balance in Chronic Congestive Heart Failure Secondary to Coronary Artery Disease, The American Journal of Cardiology, vol. 70, No. 20, pp. 1576-1582, dated Dec. 15, 1992.

Extended European Search Report issued in counterpart Europe Patent Application No. 21914281.7, dated Jun. 4, 2024.

Notice of Reasons for Refusal issued in counterpart Japanese Patent Application No. 2023-540820, dated Jul. 2, 2024.

International Search Report and Written Opinion issued in corresponding PCT Application No. PCT/CN2021/141715, dated Apr. 1, 2022.

* cited by examiner

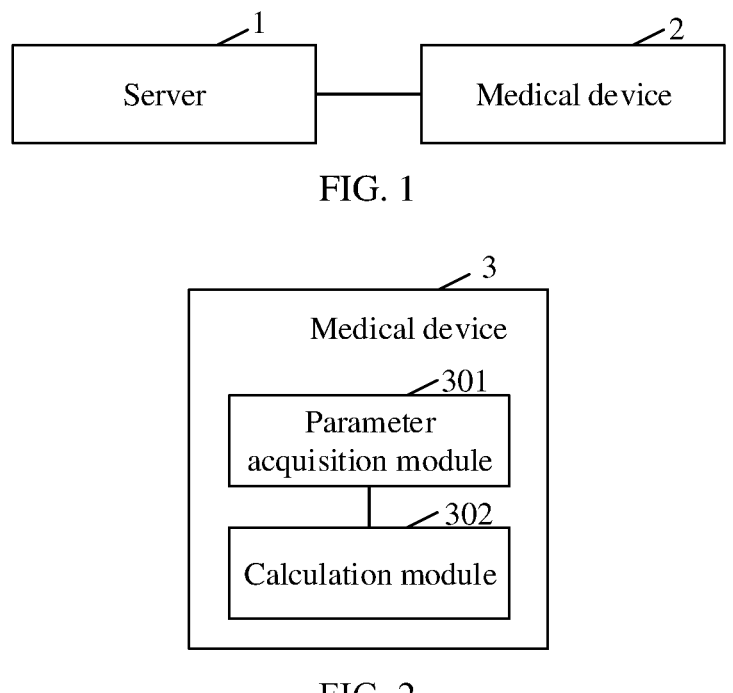

Determining, based on a preset analysis time interval, a state evaluation parameter corresponding to an object to be tested

S200

Determining, based on the state evaluation parameter, first state information corresponding to the object to be tested

Determining, based on the state evaluation parameter, numerical variation information corresponding to the object to be tested

S220

Determining, based on the numerical variation information, the first state information

FIG. 4

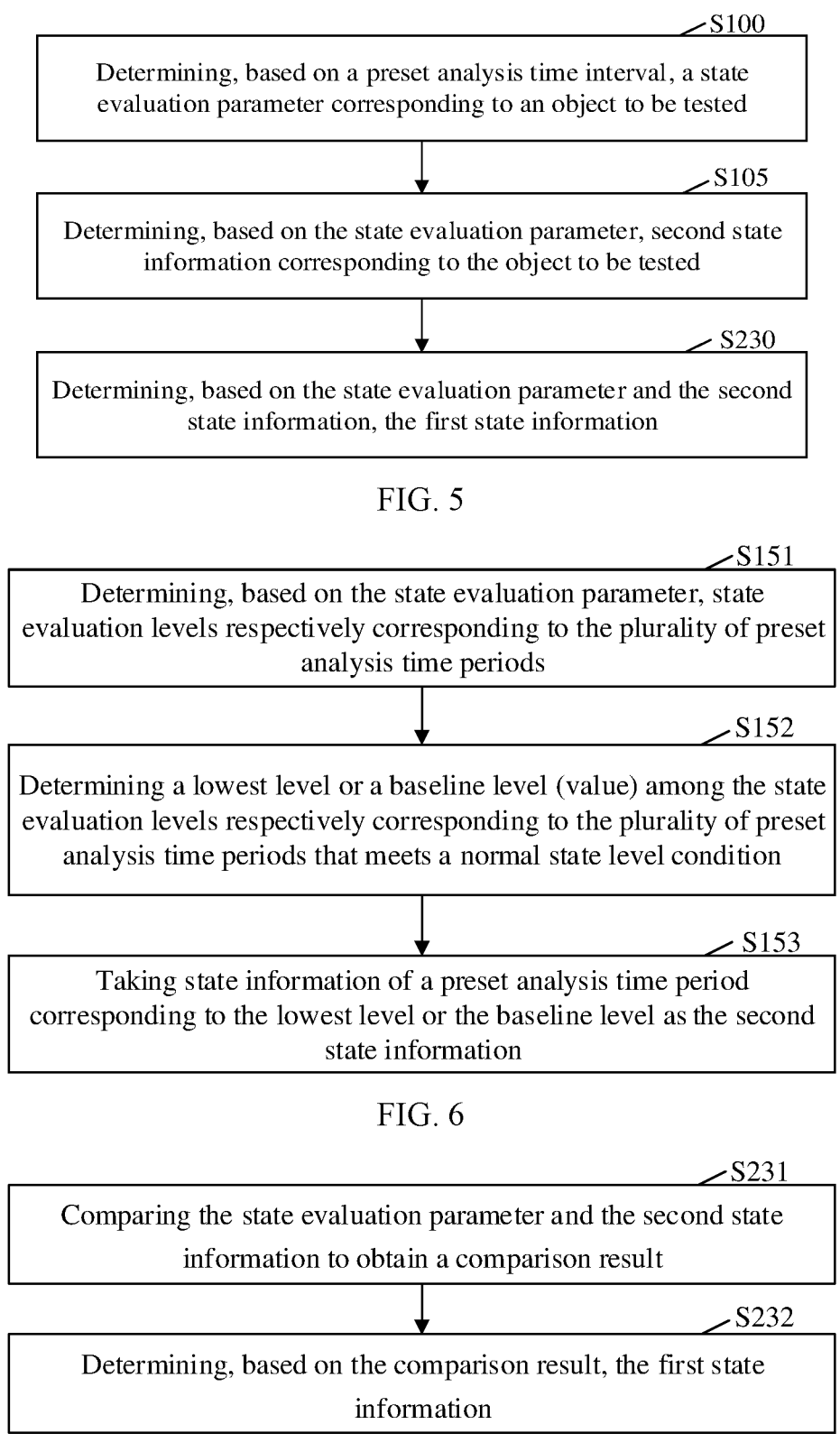

S100

Determining, based on a preset analysis time interval, a state evaluation parameter corresponding to an object to be tested

S105

Determining, based on the state evaluation parameter, second state information corresponding to the object to be tested

S230

Determining, based on the state evaluation parameter and the second state information, the first state information

Determining, based on the state evaluation parameter, state evaluation levels respectively corresponding to the plurality of preset analysis time periods

S152

Determining a lowest level or a baseline level (value) among the state evaluation levels respectively corresponding to the plurality of preset analysis time periods that meets a normal state level condition

S153

Taking state information of a preset analysis time period corresponding to the lowest level or the baseline level as the second state information

Comparing the state evaluation parameter and the second state information to obtain a comparison result

S232

Determining, based on the comparison result, the first state information

FIG. 7

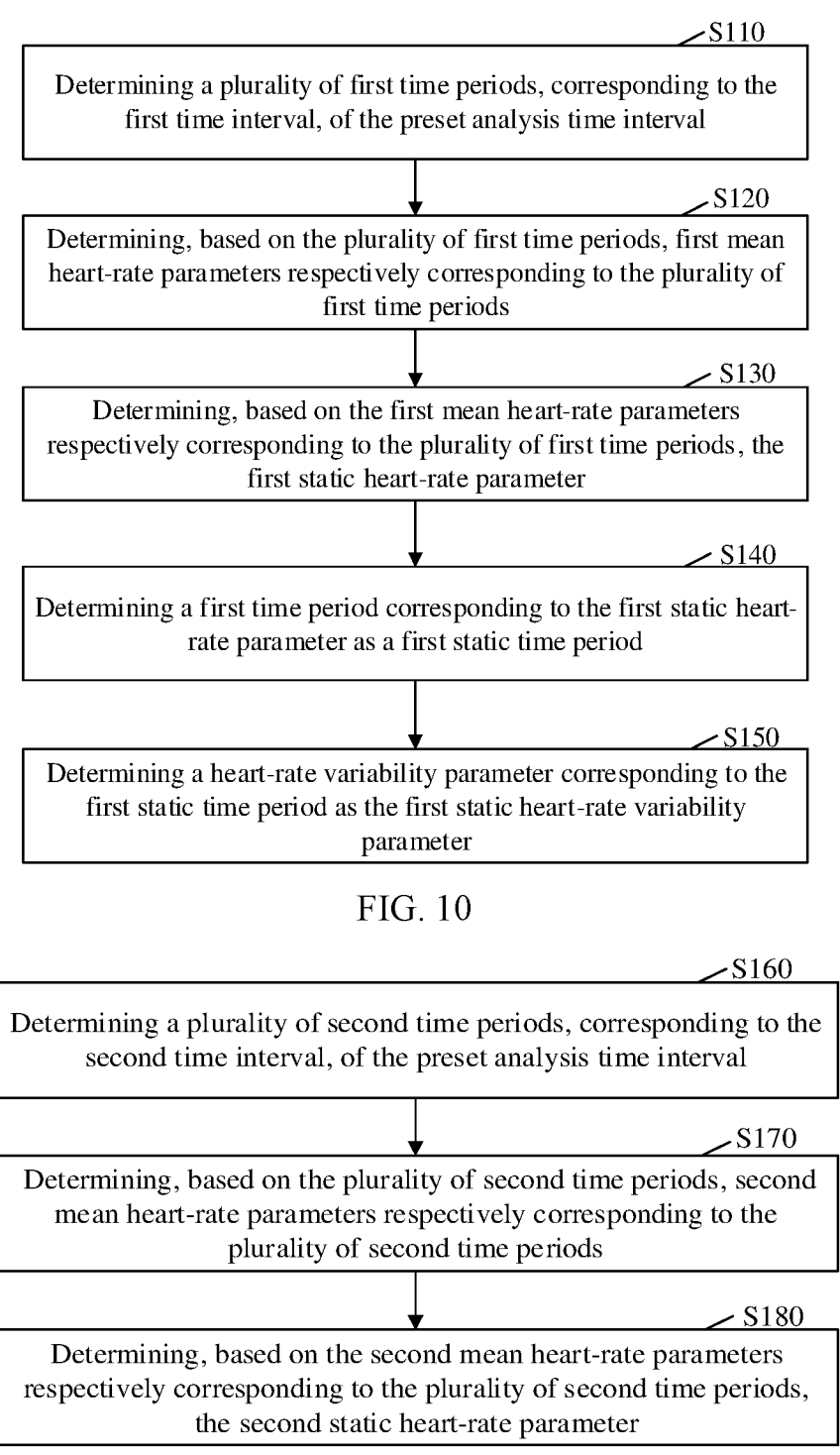

S110

Determining a plurality of first time periods, corresponding to the first time interval, of the preset analysis time interval

S120

Determining, based on the plurality of first time periods, first mean heart-rate parameters respectively corresponding to the plurality of first time periods

S130

Determining, based on the first mean heart-rate parameters respectively corresponding to the plurality of first time periods, the first static heart-rate parameter

S140

Determining a first time period corresponding to the first static heart-rate parameter as a first static time period

S150

Determining a heart-rate variability parameter corresponding to the first static time period as the first static heart-rate variability parameter

Determining a plurality of second time periods, corresponding to the second time interval, of the preset analysis time interval

S170

Determining, based on the plurality of second time periods, second mean heart-rate parameters respectively corresponding to the plurality of second time periods

S180

Determining, based on the second mean heart-rate parameters respectively corresponding to the plurality of second time periods, the second static heart-rate parameter

FIG. 11

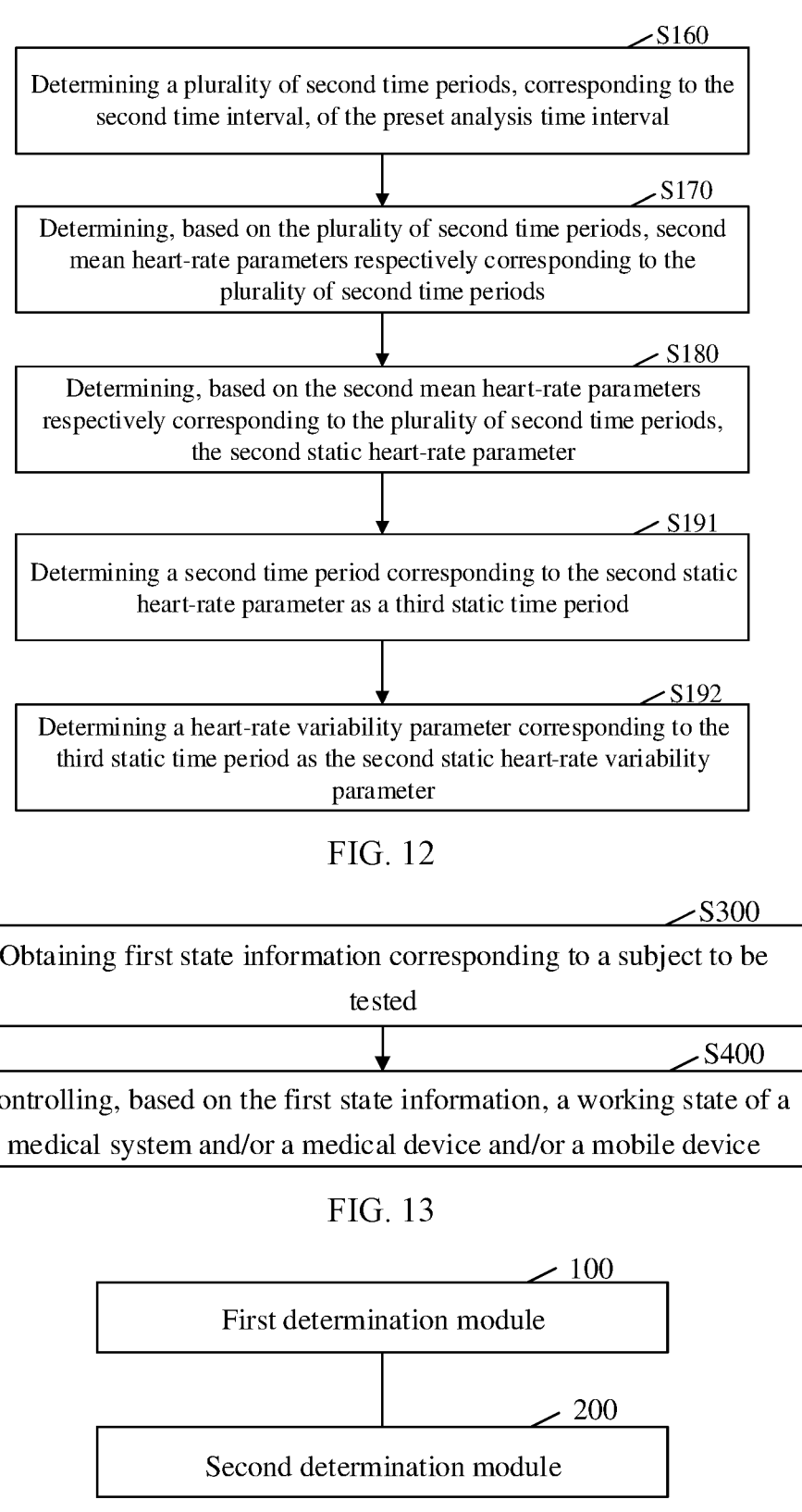

S160

Determining a plurality of second time periods, corresponding to the second time interval, of the preset analysis time interval

S170

Determining, based on the plurality of second time periods, second mean heart-rate parameters respectively corresponding to the plurality of second time periods

S180

Determining, based on the second mean heart-rate parameters respectively corresponding to the plurality of second time periods, the second static heart-rate parameter

S191

Determining a second time period corresponding to the second static heart-rate parameter as a third static time period

S192

Determining a heart-rate variability parameter corresponding to the third static time period as the second static heart-rate variability parameter

Obtaining first state information corresponding to a subject to be tested

S400

Controlling, based on the first state information, a working state of a medical system and/or a medical device and/or a mobile device

First determination module

200

Second determination module

FIG. 14

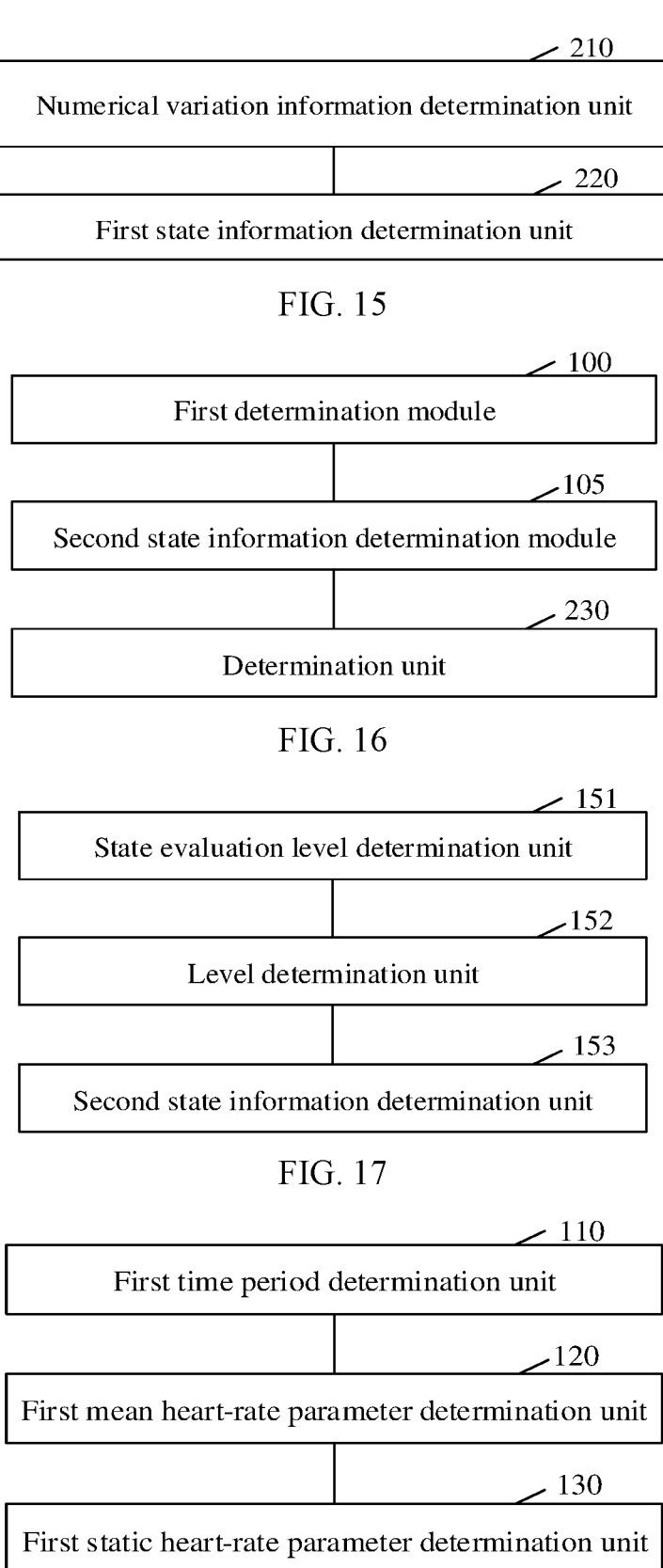

210

Numerical variation information determination unit

220

First state information determination unit

First determination module

105

Second state information determination module

230

Determination unit

State evaluation level determination unit

152

Level determination unit

153

Second state information determination unit

First time period determination unit

120

First mean heart-rate parameter determination unit

130

First static heart-rate parameter determination unit

FIG. 18

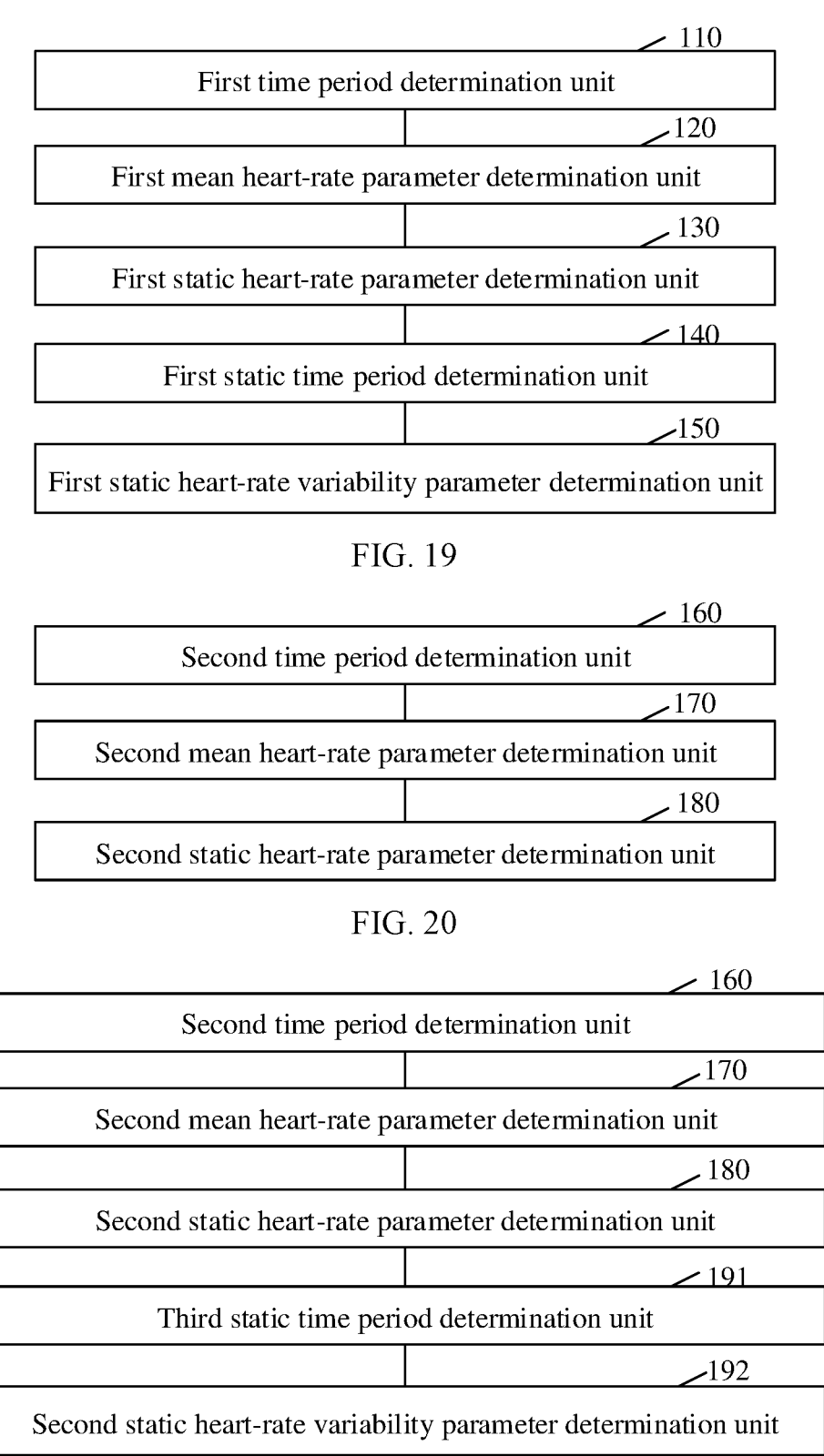

110

First time period determination unit

120

First mean heart-rate parameter determination unit

130

First static heart-rate parameter determination unit

140

First static time period determination unit

150

First static heart-rate variability parameter determination unit

Second time period determination unit

170

Second mean heart-rate parameter determination unit

180

Second static heart-rate parameter determination unit

Second time period determination unit

170

Second mean heart-rate parameter determination unit

180

Second static heart-rate parameter determination unit

191

Third static time period determination unit

192

Second static heart-rate variability parameter determination unit

FIG. 21

300
Acquisition module
400
Control module

Processor
2301

Input Device
2303

Memory 2302

Output Device
2304

Electronic Device 2300

STATE INFORMATION DETERMINATION METHOD AND DEVICE, CONTROL METHOD AND DEVICE

CROSS-REFERENCE TO RELATED APPLICATIONS

This application is a continuation of International Application No. PCT/CN2021/141715, filed on Dec. 27, 2021, which claims priority to Chinese Patent Application No. 202011624641.6, filed on Dec. 30, 2020. The disclosures of the aforementioned applications are hereby incorporated by reference in their entireties.

TECHNICAL FIELD

The present disclosure relates to the field of medical data processing technologies, and in particular, to a state information determination method and device, a control method and device, a non-transitory computer-readable storage medium and an electronic device.

BACKGROUND

As is well known, as parameters such as a heart rate and heart rate variability corresponding to a subject to be tested are easily affected by various factors such as circadian rhythm, course of disease, sleep status, and medication, it is difficult to determine state information of the subject to be tested (such as state information of neurohormone of the subject to be tested) and comparability thereof on the basis of the parameters such as heart rate and heart rate variability.

SUMMARY

To solve technical problems mentioned above, the present disclosure is proposed. A state information determination method and device, a control method and device, a non-transitory computer-readable storage medium, and an electronic device are provided by embodiments of the present disclosure.

According to an aspect, an embodiment of the present disclosure provides a state information determination method, including: determining, based on a preset analysis time interval, a state evaluation parameter corresponding to a subject to be tested; and determining, based on the state evaluation parameter, first state information corresponding to the subject to be tested. The state evaluation parameter includes at least one of a first heart-rate characterization parameter, a first heart-rate variability characterization parameter, a second heart-rate characterization parameter, and a second heart-rate variability characterization parameter, the first heart-rate characterization parameter and the first heart-rate variability characterization parameter correspond to a first time interval, and the second heart-rate characterization parameter and the second heart-rate variability characterization parameter correspond to a second time interval.

According to an embodiment of the present disclosure, the determining, based on the state evaluation parameter, first state information corresponding to the subject to be tested includes: determining, based on the state evaluation parameter, numerical variation information corresponding to the subject to be tested; and determining, based on the numerical variation information, the first state information.

According to an embodiment of the present disclosure, before the determining, based on the state evaluation parameter, first state information corresponding to the subject to be tested, the method further includes: determining, based on the state evaluation parameter, second state information corresponding to the subject to be tested, where the determining, based on the state evaluation parameter, first state information corresponding to the subject to be tested includes: determining, based on the state evaluation parameter and the second state information, the first state information.

According to an embodiment of the present disclosure, the preset analysis time interval includes a plurality of preset analysis time periods, and the determining, based on the state evaluation parameter, second state information corresponding to the subject to be tested includes: determining, based on the state evaluation parameter, state evaluation levels respectively corresponding to the plurality of preset analysis time periods; determining a lowest level or a baseline level among the state evaluation levels respectively corresponding to the plurality of preset analysis time periods that meet a normal state level condition; and taking state information of a preset analysis time period corresponding to the lowest level or the baseline level as the second state information.

According to an embodiment of the present disclosure, the determining, based on the state evaluation parameter and the second state information, the first state information includes: comparing the state evaluation parameter and the second state information to obtain a comparison result; and determining, based on the comparison result, the first state information.

According to an embodiment of the present disclosure, the state evaluation parameter includes the first heart-rate characterization parameter, the first heart-rate characterization parameter includes a first mean heart-rate parameter and a first static heart-rate parameter, and the determining, based on a preset analysis time interval, a state evaluation parameter corresponding to a subject to be tested includes: determining a plurality of first time periods, corresponding to the first time interval, of the preset analysis time interval; determining, based on the plurality of first time periods, first mean heart-rate parameters respectively corresponding to the plurality of first time periods; and determining, based on the first mean heart-rate parameters respectively corresponding to the plurality of first time periods, the first static heart-rate parameter.

According to an embodiment of the present disclosure, the determining, based on the first mean heart-rate parameters respectively corresponding to the plurality of first time periods, the first static heart-rate parameter includes: determining a minimum first mean heart-rate parameter among the first mean heart-rate parameters respectively corresponding to the plurality of first time periods; and determining the minimum first mean heart-rate parameter as the first static heart-rate parameter.

According to an embodiment of the present disclosure, the state evaluation parameter further includes the first heart-rate variability characterization parameter, the first heart-rate variability characterization parameter includes a first static heart-rate variability parameter, and after the determining, based on the first mean heart-rate parameters respectively corresponding to the plurality of first time periods, the first static heart-rate parameter, the method further includes: determining a first time period corresponding to the first static heart-rate parameter as a first static time period; and determining a heart-rate variability parameter corresponding to the first static time period as the first static heart-rate variability parameter.

According to an embodiment of the present disclosure, before the determining, based on the plurality of first time periods, first mean heart-rate parameters respectively corresponding to the plurality of first time periods, the method further includes: removing an unstable time interval corresponding to each of the plurality of first time periods, where the determining, based on the plurality of first time periods, first mean heart-rate parameters respectively corresponding to the plurality of first time periods includes: determining, based on a plurality of first time periods without the unstable time interval, the first mean heart-rate parameters respectively corresponding to the plurality of first time periods.

According to an embodiment of the present disclosure, the state evaluation parameter includes the second heart-rate characterization parameter, the second heart-rate characterization parameter includes a second mean heart-rate parameter and a second static heart-rate parameter, and the determining, based on a preset analysis time interval, a state evaluation parameter corresponding to a subject to be tested includes: determining a plurality of second time periods, corresponding to the second time interval, of the preset analysis time interval; determining, based on the plurality of second time periods, second mean heart-rate parameters respectively corresponding to the plurality of second time periods; and determining, based on the second mean heart-rate parameters respectively corresponding to the plurality of second time periods, the second static heart-rate parameter.

According to an embodiment of the present disclosure, the determining, based on the second mean heart-rate parameters respectively corresponding to the plurality of second time periods, the second static heart-rate parameter includes: determining a minimum second mean heart-rate parameter among the second mean heart-rate parameters respectively corresponding to the plurality of second time periods; and determining the minimum second mean heart-rate parameter as the second static heart-rate parameter.

According to an embodiment of the present disclosure, the second heart-rate variability characterization parameter further includes a second static heart-rate variability parameter, and after the determining, based on the second mean heart-rate parameters respectively corresponding to the plurality of second time periods, the second static heart-rate parameter, the method further includes: determining a second time period corresponding to the second static heart-rate parameter as a third static time period; and determining a heart-rate variability parameter corresponding to the third static time period as the second static heart-rate variability parameter.

According to an embodiment of the present disclosure, before the determining, based on the plurality of second time periods, second mean heart-rate parameters respectively corresponding to the plurality of second time periods, the method further includes: removing an unstable time interval corresponding to each of the plurality of second time periods, where the determining, based on the plurality of second time periods, second mean heart-rate parameters respectively corresponding to the plurality of second time periods includes: determining, based on a plurality of second time periods without the unstable time interval, the second mean heart-rate parameters respectively corresponding to the plurality of second time periods.

According to an embodiment of the present disclosure, the first state information is state information of a neuro-hormonal activity of the subject to be tested.

According to another aspect, an embodiment of the present disclosure provides a control method, including: obtaining first state information corresponding to a subject to be tested, where the first state information is obtained based on the state information determination method provided by any one of embodiments described above; and controlling, based on the first state information, a working state of a medical system and/or a medical device and/or a mobile device.

According to another aspect, an embodiment of the present disclosure provides a state information determination device, including: a first determination module, configured to determine, based on a preset analysis time interval, a state evaluation parameter corresponding to a subject to be tested, where the state evaluation parameter includes at least one of a first heart-rate characterization parameter, a first heart-rate variability characterization parameter, a second heart-rate characterization parameter, and a second heart-rate variability characterization parameter, the first heart-rate characterization parameter and the first heart-rate variability characterization parameter correspond to a first time interval, and the second heart-rate characterization parameter and the second heart-rate variability characterization parameter correspond to a second time interval; and a second determination module, configured to determine, based on the state evaluation parameter, first state information corresponding to the subject to be tested.

According to another aspect, an embodiment of the present disclosure provides a control device, including: an acquisition module, configured to acquire first state information corresponding to a subject to be tested, where the first state information is obtained based on the state information determination method provided by any one of embodiments described above; and a control module, configured to control, based on the first state information, a working state of a medical system and/or a medical device.

According to another aspect, an embodiment of the present disclosure provides a non-transitory computer-readable storage medium, where a computer program is stored for performing the state information determination method and/or the control method provided by embodiments described above.

According to another aspect, an embodiment of the present disclosure provides an electronic device, including: a processor; and a memory, configured to store executable instructions of the processor, where the processor is configured to implement the state information determination method and/or the control method provided by embodiments described above.

First state information corresponding to a subject to be tested is not directly determined based on a heart rate and/or a heart rate variability parameter corresponding to the subject to be tested in the present disclosure, but is determined by utilizing a state evaluation parameter corresponding to the subject to be tested. Thus, accuracy and comparability at different times of determined first state information may be improved, thereby providing favorable conditions for assisting in predicting disease progress of the subject to be tested and other situations on the basis of the determined first state information.

BRIEF DESCRIPTION OF THE DRAWINGS

Through a more detailed description of embodiments of the present disclosure with reference to accompanying drawings, the present disclosure described above and other objects, features, and advantages of the present disclosure may become more apparent. The accompanying drawings are used to provide a further understanding of the embodiments of the present disclosure, and constitute a part of specification for explaining the present disclosure together with the embodiments of the present disclosure, and do not constitute a limitation on the present disclosure. In the accompanying drawings, the same reference numerals generally represent the same component or step.

FIG. 1 is a schematic diagram of an applicable scenario of an embodiment of the present disclosure.

FIG. 2 is a schematic diagram of another applicable scenario of an embodiment of the present disclosure.

FIG. 3 is a schematic flowchart of a state information determination method according to an exemplary embodiment of the present disclosure.

FIG. 4 is a schematic flowchart of a method for determining, based on the state evaluation parameter, first state information corresponding to a subject to be tested according to an exemplary embodiment of the present disclosure.

FIG. 5 is a schematic flowchart of a state information determination method according to another exemplary embodiment of the present disclosure.

FIG. 6 is a schematic flowchart of a method for determining, based on a state evaluation parameter, second state information corresponding to a subject to be tested according to an exemplary embodiment of the present disclosure.

FIG. 7 is a schematic flowchart of a method for determining, based on a state evaluation parameter and second state information, first state information according to an exemplary embodiment of the present disclosure.

FIG. 10 is a schematic flowchart of a method for determining, based on a preset analysis time interval, a state evaluation parameter corresponding to a subject to be tested according to another exemplary embodiment of the present disclosure.

FIG. 11 is a schematic flowchart of a method for determining, based on a preset analysis time interval, a state evaluation parameter corresponding to a subject to be tested according to still another exemplary embodiment of the present disclosure.

FIG. 12 is a schematic flowchart of a method for determining, based on a preset analysis time interval, a state evaluation parameter corresponding to a subject to be tested according to yet another exemplary embodiment of the present disclosure.

FIG. 13 is a schematic flowchart of a control method according to an exemplary embodiment of the present disclosure.

FIG. 14 is a schematic structural diagram of a state information determination device according to an exemplary embodiment of the present disclosure.

FIG. 15 is a schematic structural diagram of a second determination module according to an exemplary embodiment of the present disclosure.

FIG. 16 is a schematic structural diagram of a state information determination device according to another exemplary embodiment of the present disclosure.

FIG. 17 is a schematic structural diagram of a second state information determination module according to an exemplary embodiment of the present disclosure.

FIG. 18 is a schematic structural diagram of a first determination module according to an exemplary embodiment of the present disclosure.

FIG. 19 is a schematic structural diagram of a first determination module according to another exemplary embodiment of the present disclosure.

FIG. 20 is a schematic structural diagram of a first determination module according to still another exemplary embodiment of the present disclosure.

FIG. 21 is a schematic structural diagram of a first determination module according to yet another exemplary embodiment of the present disclosure.

DETAILED DESCRIPTION OF THE EMBODIMENTS

Figures 8, 9:
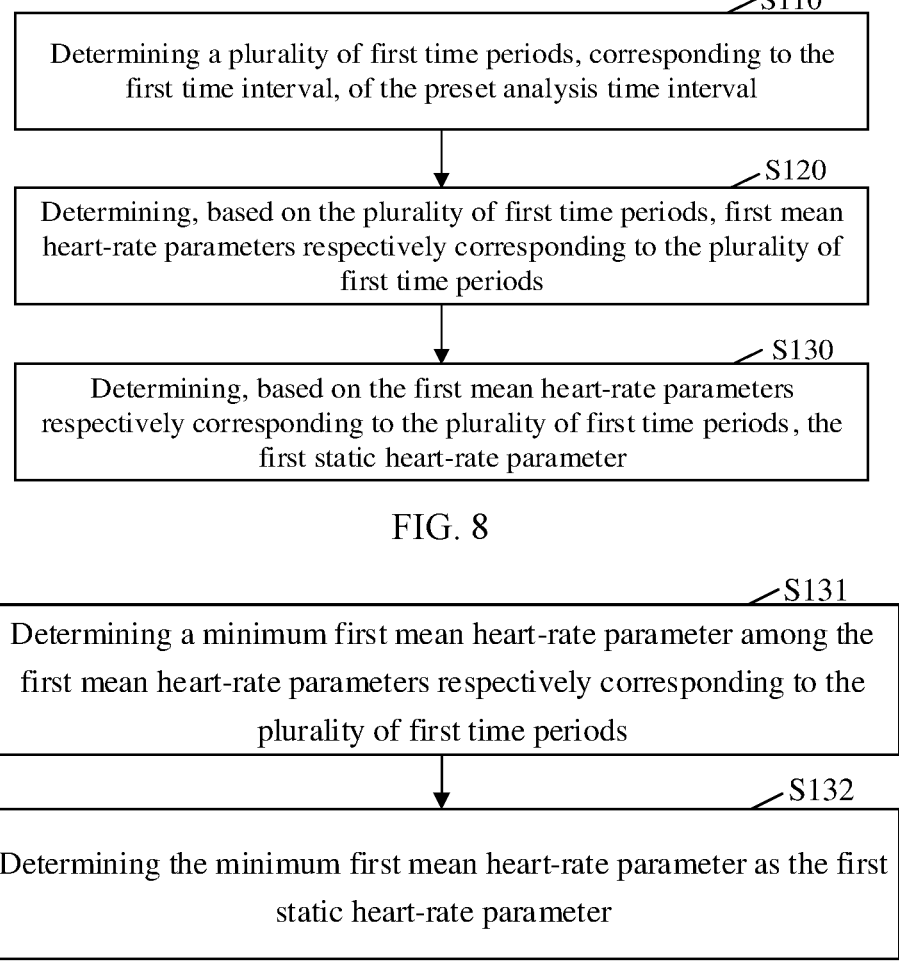
FIG. 8 is a schematic flowchart of a method for determining, based on a preset analysis time interval, a state evaluation parameter corresponding to a subject to be tested according to an exemplary embodiment of the present disclosure.
FIG. 9 is a schematic flowchart of a method for determining, based on first mean heart-rate parameters respectively corresponding to a plurality of first time periods, a first static heart-rate parameter according to an exemplary embodiment of the present disclosure.

Hereinafter, exemplary embodiments provided by the present disclosure are described in detail with reference to accompanying drawings. Apparently, described embodiments are only a part, but not all, of the embodiments of the present disclosure, and it should be understood that the present disclosure is not limited by the exemplary embodiments described herein.

Overview

As is well known, neurohormones driven by sympathetic and parasympathetic nerves are highly susceptible to various factors. Especially for heart disease patients with heart failure or arrhythmia, their neurohormones are highly susceptible to factors such as circadian rhythm, course of disease, sleep status, exercise or activity levels, body position, medication, emotional changes and the like. Therefore, in the prior art, heart rate (HR) and heart rate variability (HRV) are usually used as diagnostic criteria or alternative measurement indicators to characterize neurohormones. Specifically, the heart rate refers to a number of heartbeats per minute. The heart rate variability refers to changes in differences between successive heartbeat cycles. Sources for heart rate calculation include but are not limited to body surface electrocardiogram, endocardium, epicardium electrocardiogram, electrocardiogram from a subcutaneous electrode, or ventricular heart rate or atrial heart rate calculated by R wave and P wave. Moreover, it should be understood that heart rate may also be calculated by using other techniques, such as but not limited to photoplethysmography (PPG).

However, both the heart rate and the heart rate variability are still highly susceptible. For example, the heart rate and/or the heart rate variability often change during different sleep stages at night, and this change may not necessarily be related to neurohormones. Meanwhile, states during different sleep stages at night are not always repeated. Moreover, due to a low heart rate, a patient equipped with a pacemaker or an implantable cardioverter defibrillator (ICD) usually has pace-making at night; in this case, the patient's real heart rate is usually "hidden", so that a real heart rate would not be reflected in the measured heart rate data. Furthermore, in the prior arts, daytime heart rate and daytime heart rate variability measured also include data obtained during exercise or during emotional arousal phases or at different body positions. However, the data obtained during exercise and emotional arousal phases may only characterize short-term states, and these short-term changes are different at different times (days). Meanwhile, diseases such as heart failure have a significant impact on the patient's level and/or state of neurohormone, but the impact is relatively long-term in terms of time. It can be seen that it is difficult to determine state information of the subject to be tested (such as state information of neurohormone of the subject to be tested) on the basis of the parameters such as heart rate and heart rate variability in the conventional arts.

Based on the aforementioned technical problems, a basic concept of the present disclosure is to propose a state information determination method and device, a control method and device, a non-transitory computer-readable storage medium and an electronic device.

A state information determination method provided by the present disclosure includes: determining, based on a preset analysis time interval, a state evaluation parameter corresponding to a subject to be tested, where the state evaluation parameter includes at least one of a first heart-rate characterization parameter, a first heart-rate variability characterization parameter, a second heart-rate characterization parameter, and a second heart-rate variability characterization parameter, the first heart-rate characterization parameter and the first heart-rate variability characterization parameter correspond to a first time interval, and the second heart-rate characterization parameter and the second heart-rate variability characterization parameter correspond to a second time interval; and determining, based on the state evaluation parameter, first state information corresponding to the subject to be tested.

First state information corresponding to a subject to be tested is not directly determined based on a heart rate and/or a heart rate variability parameter corresponding to the subject to be tested in the present disclosure, but is determined by utilizing a state evaluation parameter corresponding to the subject to be tested. Thus, accuracy and comparability at different times of determined first state information may be improved, thereby providing favorable conditions for assisting in predicting disease progress of the subject to be tested and other situations on the basis of the determined first state information.

After the basic principles of the present disclosure are introduced, a specific introduction of various non limiting embodiments of the present disclosure is given below with reference to accompanying drawings.

Exemplary Scenario

FIG. 1 is a schematic diagram of an applicable scenario of an embodiment of the present disclosure. As shown in FIG. 1, the scenario where embodiments of the present disclosure are applicable to includes a server 1 and a medical device 2. The server 1 and the medical device 2 are connected through communication.

Specifically, the medical device 2 is used to collect a criterion parameter of the subject to be tested, including but not limited to a heart-rate parameter and a heart-rate variability parameter. The server 1 is used to determine, based on a preset analysis time interval, a state evaluation parameter corresponding to the subject to be tested, and to determine, based on the state evaluation parameter, first state information corresponding to the subject to be tested. The state evaluation parameter includes at least one of a first heart-rate characterization parameter, a first heart-rate variability characterization parameter, a second heart-rate characterization parameter, and a second heart-rate variability characterization parameter, the first heart-rate characterization parameter and the first heart-rate variability characterization parameter correspond to a first time interval, and the second heart-rate characterization parameter and the second heart-rate variability characterization parameter correspond to a second time interval. That is, a state information determination method is implemented in this scenario.

Exemplarily, the server 1 determines, based on the criterion parameter collected by the medical device 2, the state evaluation parameter mentioned above.

Furthermore, the server 1 is also used to acquire first state information corresponding to a subject to be tested, and control, based on the first state information, a working state of a medical system and/or the medical device 2 and/or a mobile device. That is, a control method is implemented in this scenario.

As the state information determination method and/or a control method are realized through the server 1 according to the above scenario shown in FIG. 1, not only adaptability to different scenarios is improved, but also a computational complexity of the medical device 2 is effectively reduced.

It should be noted that the present disclosure also applies to another scenario. FIG. 2 is a schematic diagram of another applicable scenario of an embodiment of the present disclosure. Specifically, this scenario includes a medical device 3, and the medical device 3 includes a parameter acquisition module 301 and a calculation module 302.

Specifically, the parameter acquisition module 301 in the medical device 3 is used to collect criterion parameters of a subject to be tested, including but not limited to a heart-rate parameter, a heart-rate variability parameter, and the like. The calculation module 302 is used to determine, based on a preset analysis time interval, a state evaluation parameter corresponding to the subject to be tested, and to determine, based on the state evaluation parameter, first state information corresponding to the subject to be tested. The state evaluation parameter includes at least one of a first heart-rate characterization parameter, a first heart-rate variability characterization parameter, a second heart-rate characterization parameter, and a second heart-rate variability characterization parameter. The first heart rate characterization parameter and the first heart rate variability characterization parameter correspond to a first time interval, and the second heart rate characterization parameter and the second heart rate variability characterization parameter correspond to a second time interval. That is, a state information determination method is implemented in this scenario.

Exemplarily, the calculation module 302 determines, based on the criterion parameter collected by the parameter acquisition module 301, the state evaluation parameter mentioned above.

Furthermore, the calculating module 302 is also used to acquire first state information corresponding to a subject to be tested, and to control, based on the first state information, a working state of a medical system and/or the medical device 3 and/or a mobile device. That is, a control method is implemented in this scenario.

As the state information determination method and/or the control method are realized through the medical device 3 in the scenario described above shown in FIG. 2, there is no need for data transmission operations with servers and other related devices. Therefore, the above scenario can ensure a real-time performance of the state information determination method and/or the control method.

It should be noted that the medical devices mentioned in the above scenarios may be either Implantable Medical Devices (IMD) or Wearable Medical Devices (WMD), and are not uniformly limited in the present disclosure.

Exemplary Method

FIG. 3 is a schematic flowchart of a state information determination method according to an exemplary embodiment of the present disclosure. As shown in FIG. 3, a state information determination method according to the embodiment of the present disclosure includes the following steps.

Step S100: determining, based on a preset analysis time interval, a state evaluation parameter corresponding to a subject to be tested.

In the embodiment of the present disclosure, the state evaluation parameter includes at least one of a first heart-rate characterization parameter, a first heart-rate variability characterization parameter, a second heart-rate characterization parameter, and a second heart-rate variability characterization parameter, the first heart-rate characterization parameter and the first heart-rate variability characterization parameter correspond to a first time interval, and the second heart-rate characterization parameter and the second heart-rate variability characterization parameter correspond to a second time interval.

Exemplarily, the first time interval includes a nighttime interval. For example, in a 24-hour system, the first time interval is from 18:00 of a current day to 6:00 of a next day. Optionally, the first time interval is from 22:00 of a current day to 6:00 of a next day. Optionally, during the first time interval, the subject to be tested is in a resting or sleeping state to reduce interference, thereby improving accuracy of the state evaluation parameter obtained finally. The resting state refers to a state in which a body is relatively at rest, while the sleeping state refers to a state of being asleep, where a body is still, and in a "lying" posture.

Exemplarily, the second time interval includes a daytime interval. For example, in the 24-hour system, the second time interval is from 6:00 to 18:00 of a current day. Optionally, the second time interval is from 8:00 to 20:00 of a current day. Optionally, during the second time interval, the subject to be tested is in a resting state, or almost has no movement or activity to reduce interference, thereby improving accuracy and comparability of the state evaluation parameter obtained finally. Optionally, during the second time interval, the subject to be tested is at rest or at a non-motion state with a non-standing position. Exemplarily, the non-motion state mentioned above may be determined through some relevant motion/body movement or other physiological parameter thresholds. For example, if a real-time motion signal of the subject to be tested is below a certain threshold, or if a real-time heart rate of the subject to be tested does not exceed a preset exercise heart-rate threshold, it can be determined that the subject to be tested is at the non-motion state.

Exemplarily, the subject to be tested mentioned in Step S100 refers to a human body. That is, a state evaluation parameter corresponding to a human body is determined. It should be understood that the determining a state evaluation parameter corresponding to a subject to be tested mentioned in Step S100 may mean calculating the state evaluation parameter corresponding to the subject to be tested.

It should be noted that, the preset analysis time interval mentioned in step S100 may include one or more of first time intervals and/or one or more of second time intervals. For example, the preset analysis time interval may be a one-week time interval including seven natural days.

Step S200: determining, based on the state evaluation parameter, first state information corresponding to the subject to be tested.

Exemplarily, the first state information mentioned in step S200 refers to information capable of characterizing a state condition (such as a state condition of a heart) corresponding to a subject to be tested. For example, the first state information may be absolute trend variation information and/or relative trend variation information, determined based on a state evaluation parameter and corresponding to the state evaluation parameter. The absolute trend variation information may be numerical information which may change over time, and the relative trend variation information may be numerical information which may change relative to a baseline value.

In practical applications, based on the preset analysis time interval, the state evaluation parameter corresponding to a subject to be tested is determined, and based on the state evaluation parameter, the first state information corresponding to the subject to be tested is determined.

First state information corresponding to a subject to be tested is not directly determined based on a heart rate and/or a heart rate variability parameter corresponding to the subject to be tested in the present disclosure, but is determined by utilizing a state evaluation parameter corresponding to the subject to be tested. Thus, accuracy and comparability at different times of determined first state information may be improved, thereby providing favorable conditions for assisting in predicting disease progress of the subject to be tested and other situations on the basis of the determined first state information.

FIG. 4 is a schematic flowchart of a method for determining, based on the state evaluation parameter, first state information corresponding to a subject to be tested according to an exemplary embodiment of the present disclosure. The embodiment shown in FIG. 4 is an extension of the embodiment shown in FIG. 3. Differences between the embodiment shown in FIG. 4 and the embodiment shown in FIG. 3 will be introduced below, and similarities will not be described herein again.

As shown in FIG. 4, according to state information determination method provided by an embodiment of the present disclosure, the step of determining, based on the state evaluation parameter, first state information corresponding to a subject to be tested includes the following steps.

Step S210: determining, based on the state evaluation parameter, numerical variation information corresponding to the subject to be tested.

Exemplarily, the numerical variation information includes absolute-numerical variation trend information. For example, the absolute-numerical variation trend information includes an absolute rising trend within a preset time range, an absolute falling trend within the preset time range, and a relatively stable trend within the preset time range.

In an embodiment of the present disclosure, a means of linear regression (absolute value and time) may be used to calculate a trend line capable of characterizing absolute-value variation information mentioned above. Other statistical analysis methods may also be used similarly.

For example, the state evaluation parameter includes a first heart-rate characterization parameter, and the first heart-rate characterization parameter includes a first mean heart-rate parameter and a first static heart-rate parameter. Then, correspondingly, the absolute-numerical variation trend information may include absolute-numerical variation trend information of the first mean heart-rate parameter and absolute-numerical variation trend information of the first static heart-rate parameter, or a variation trend of a combination of the absolute value of the first mean heart-rate parameter and the absolute value of the first static heart-rate parameter.

It should be understood that the state evaluation parameter is not limited to the first mean heart-rate parameter and the first static heart-rate parameter mentioned above, specific parameters included in the state evaluation parameter, and specific characterization meaning of each parameter may be referred to following embodiments (such as embodiments in FIG. 8 to FIG. 12).

Exemplarily, numerical variation trend information is relationship information between a certain correlation coefficient of a state evaluation parameter and a corresponding preset coefficient threshold. For another example, numerical variation trend information is relationship information between a slope value (or a mean value) of a state evaluation parameter and a corresponding preset slope value threshold (or a preset mean value threshold). Optionally, when a slope value (or mean value) of a state evaluation parameter is less than a corresponding preset slope value threshold value (or a preset mean value threshold value), the absolute-numerical variation trend information of a state evaluation parameter may be defined as a downward trend within a preset time range.

It should be noted that specific values of the preset coefficient threshold value, the preset slope value threshold value, and the preset mean value threshold value mentioned above may be set according to actual situations, and these are not uniformly limited in the embodiments of the present disclosure.

Step S220: determining, based on the numerical variation information, the first state information.

For example, if the numerical variation information includes the numerical variation trend information, then correspondingly, determined first state information may be state information related to "a rising trend within a preset time range".

In an embodiment of the present disclosure, the numerical variation trend includes three types of "rising", "falling" and "stable". In a relatively simple situation, for example, when the numerical value corresponds to heart rate variability, the three trends respectively correspond to three states of "getting better", "getting worse" and "stable" of a subject. When the numerical value corresponds to a static heart rate, the three trends respectively correspond to three states of "getting better", "getting worse" and "stable" of a subject. If the numerical value corresponds to a certain combination of the heart rate variability and the static heart rate, the three trends may correspond to three states according to a combined specific algorithm.

According to the state information determination method provided by the embodiment of the present disclosure, numerical variation information corresponding to a subject to be tested is determined based on a state evaluation parameter, and first state information is determined based on the numerical variation information, so that a purpose of determining, based on a state evaluation parameter, first state information corresponding to the subject to be tested is realized. As the numerical variation information may reflect a real state condition of the subject to be tested to a certain extent, the embodiment of the present disclosure may effectively reduce a difference between determined first state information and a real state, thereby improving true extent of the determined first state information.

FIG. 5 is a schematic flowchart of a state information determination method according to another exemplary embodiment of the present disclosure. The embodiment shown in FIG. 5 is an extension of the embodiment shown in FIG. 3. Differences between the embodiment shown in FIG. 5 and the embodiment shown in FIG. 3 will be introduced below, and similarities will not be described herein again.

As shown in FIG. 5, in the state information determination method according to the embodiment of the present disclosure, before the step of determining, based on a state evaluation parameter, first state information corresponding to a subject to be tested, the method further includes the following steps.

Step S105: determining, based on the state evaluation parameter, second state information corresponding to the subject to be tested.

Exemplarily, the second state information mentioned in step S105 is normal state information corresponding to a subject to be tested. Correspondingly, the first state information mentioned in step S230 below is real-time state information corresponding to the subject to be tested. Optionally, the normal state information refers to state information corresponding to conditions when a subject to be tested is in a state of health, or a stable state of disease, or a state when a disease condition does not change greatly.

In addition, in the state information determination method according to the embodiment of the present disclosure, a step of determining, based on a state evaluation parameter, first state information corresponding to a subject to be tested includes the following step.

Step S230: determining, based on the state evaluation parameter and the second state information, the first state information.

In practical applications, firstly, a state evaluation parameter corresponding to a subject to be tested is determined based on a preset analysis time interval, and then the first state information corresponding to the subject to be tested is determined based on a state evaluation parameter and second state information.

Compared with the embodiment shown in FIG. 3, the embodiment of the present disclosure combines determined second state information to assist in determining the first state information. Compared with the first state information determined based on a state evaluation parameter alone, accuracy of determined first state information may be further improved according to the embodiment of the present disclosure. In particular, when the second state information is state information corresponding to "normal state" or a stable state of a disease of a subject to be tested, the embodiment of the present disclosure may fully consider an individual characteristic of the subject to be tested, thereby improving the accuracy of the determined first state information.

FIG. 6 is a schematic flowchart of a method for determining, based on a state evaluation parameter, second state information corresponding to a subject to be tested according to an exemplary embodiment of the present disclosure. The embodiment shown in FIG. 6 is an extension of the embodiment shown in FIG. 5. Differences between the embodiment shown in FIG. 6 and the embodiment shown in FIG. 5 will be introduced below, and similarities will not be described herein again.

As shown in FIG. 6, in the state information determination method according to the embodiment of the present disclosure, the preset analysis time interval includes a plurality of preset analysis time periods. And the step of determining, based on a state evaluation parameter, second state information corresponding to a subject to be tested includes the following steps.

Step S151: determining, based on the state evaluation parameter, state evaluation levels respectively corresponding to the plurality of preset analysis time periods.

Exemplarily, a preset analysis time period mentioned above is a time window with a preset time length.

It should be noted that the state evaluation level mentioned above may be set according to a specific value of a state evaluation parameter corresponding to each of the preset analysis time periods.

Step S152: determining a lowest level or a baseline level (value) among the state evaluation levels respectively corresponding to the plurality of preset analysis time periods that meet a normal state level condition.

Exemplarily, the normal state level condition mentioned in step S152 refers to a normal state level with universality. For example, if a subject to be tested is an adult, the normal state level is a normal state level corresponding to the adult. Alternatively, if a subject to be tested is a patient (such as a patient with chronic heart failure), and a "normal state" level is a disease stable state level corresponding to the patient. The state information in this state becomes a baseline level (value). In an embodiment of the present disclosure, the state information of a baseline level may be determined by a doctor or other related personnel by determining a state of a patient, or may be obtained by collecting a disease condition, a medication condition, and/or remote patient information (such as weight, symptom and the like) of the patient and then using a certain algorithm. One of collecting methods of a disease condition and a medication condition of a patient may be automatically or manually collected through a HIS system or a patient electronic case in a hospital.

Optionally, the normal state level mentioned in step S152 corresponds to the state evaluation level mentioned in step S151, so that the state evaluation level mentioned in step S151 may be discriminated based on the normal state level mentioned in step S152.

In another embodiment of the present disclosure, the step of determining a lowest level or a baseline level among the state evaluation levels respectively corresponding to the plurality of preset analysis time periods that meet a normal state level condition includes: determining, in the state evaluation levels respectively corresponding to the plurality of preset analysis time periods, a lowest level or a baseline level (value) among state evaluation levels that continuously meets the normal state level condition.

Step S153: taking state information of a preset analysis time period corresponding to the lowest level or the baseline level as second state information.

As the state information of a preset analysis time period corresponding to the lowest level or a baseline level that meets a normal state level condition is taken as the second state information, accuracy of determined second state information may be greatly improved, probability of misjudgment may be reduced, and finally accuracy of the first state information determined based on the state evaluation parameter and the second state information may be improved.

FIG. 7 is a schematic flowchart of a method for determining, based on a state evaluation parameter and second state information, first state information according to an exemplary embodiment of the present disclosure. The embodiment shown in FIG. 7 is an extension of the embodiment shown in FIG. 5. Differences between the embodiment shown in FIG. 7 and the embodiment shown in FIG. 5 will be introduced below, and similarities will not be described herein again.

As shown in FIG. 7, in the state information determination method according to the embodiment of the present disclosure, the step of determining, based on the state evaluation parameter and the second state information, the first state information includes the following steps.

Step S231: comparing the state evaluation parameter and the second state information to obtain a comparison result.

Step S232: determining, based on the comparison result, the first state information.

According to the embodiment of the present disclosure, by comparing the state evaluation parameter and the second state information, a comparison result is obtained, and then the first state information is determined based on the comparison result, so that a purpose of determining, based on the state evaluation parameter and the second state information, the first state information is achieved.

FIG. 8 is a schematic flowchart of a method for determining, based on a preset analysis time interval, a state evaluation parameter corresponding to a subject to be tested according to an exemplary embodiment of the present disclosure. The embodiment shown in FIG. 8 is an extension of the embodiment shown in FIG. 3. Differences between the embodiment shown in FIG. 8 and the embodiment shown in FIG. 3 will be introduced below, and similarities will not be described herein again.

As shown in FIG. 8, in the state information determination method according to the embodiment of the present disclosure, the state evaluation parameter includes a first heart-rate characterization parameter, and the first heart-rate characterization parameter includes a first mean heart-rate parameter and a first static heart-rate parameter. And the step of determining, based on a preset analysis time interval, a state evaluation parameter corresponding to a subject to be tested includes the following steps.

Step S110: determining a plurality of first time periods, corresponding to the first time interval, of the preset analysis time interval.

Exemplarily, a first time period is a time window with a time length of 60 seconds.

Step S120: determining, based on the plurality of first time periods, first mean heart-rate parameters respectively corresponding to the plurality of first time periods.

In other words, step S110 and step 120 refer to determining, based on a plurality of time windows respectively corresponding to the plurality of first time periods included in the preset analysis time interval, a first mean heart-rate parameter corresponding to each of the plurality of time windows.

Optionally, the first mean heart-rate (MHR) parameter corresponding to each of the plurality of time windows refers to a mean heart-rate value measured in each of the plurality of time windows.

Step S130: determining, based on the first mean heart-rate parameters respectively corresponding to the plurality of first time periods, the first static heart-rate parameter.

In an embodiment of the present disclosure, the first static heart-rate parameter is a sleep rest heart-rate (Sleep RHR) parameter.

As the first static heart-rate parameter is determined based on the first mean heart-rate parameters respectively corresponding to the plurality of first time periods, the first static heart-rate parameter obtained may fully consider characteristics of the first mean heart-rate parameters respectively corresponding to the plurality of first time periods. In view of this, the first static heart-rate parameter obtained may better characterize a heart rate condition of a subject to be tested in the first time interval.

Compared with a real-time heart rate, the first mean heart-rate parameters and the first static heart-rate parameter may more accurately characterize the heart rate condition of the subject to be tested in the first time interval. Thus, when a neurohormone level and/or state (namely, the first state information) of the subject to be tested in the first time interval is predicted based on the first mean heart-rate parameters and the first static heart-rate parameter obtained according to the embodiment of the present disclosure, a more accurate neurohormone prediction result may be obtained.

Another embodiment of the present disclosure is extended on the basis of the embodiment shown in FIG. 8. In the embodiment of the present disclosure, before the step of determining a plurality of first time periods, corresponding to a first time interval, of a preset analysis time interval, the method further includes: removing an unstable time interval corresponding to each of the plurality of first time periods. The step of determining, based on the plurality of first time periods, first mean heart-rate parameters respectively corresponding to the plurality of first time periods includes: determining, based on a plurality of first time periods without the unstable time interval, the first mean heart-rate parameters respectively corresponding to the plurality of first time periods.

Exemplarily, the unstable time interval refers to, for example, a time interval of snoring and/or a time interval of unstable respiratory rate (such as, sleep apnea).

According to an embodiment of the present disclosure, the unstable time interval also includes a time interval corresponding to special stages of sleep with high physical activity. The special stage of sleep is, for example, a Rapid Eye Movement (REM) stage, or a stage when heart rate significant changes during dreaming. And the unstable time interval also includes, for example, time intervals respectively corresponding to events such as premature atrial premature contraction (PAC), premature ventricular contraction (PVC) and atrial tachycardia or atrial arrhythmia (such as atrial fibrillation), and ventricular tachycardia (VT).

As specificity of the unstable time is relatively high, which cannot effectively characterize typical situations of the subject to be tested, the embodiment of the present disclosure may improve a characterization ability of the first mean heart-rate parameter and first static heart-rate variability parameter determined by removing the unstable time interval.

FIG. 9 is a schematic flowchart of a method for determining, based on first mean heart-rate parameters respectively corresponding to a plurality of first time periods, a first static heart-rate parameter according to an exemplary embodiment of the present disclosure. The embodiment shown in FIG. 9 is an extension of the embodiment shown in FIG. 8. Differences between the embodiment shown in FIG. 9 and the embodiment shown in FIG. 8 will be introduced below, and similarities will not be described herein again.

As shown in FIG. 9, in the state information determination method according to the embodiment of the present disclosure, the step of determining, based on the first mean heart-rate parameters respectively corresponding to the plurality of first time periods, the first static heart-rate parameter includes the following steps.

Step S131: determining a minimum first mean heart-rate parameter among the first mean heart-rate parameters respectively corresponding to the plurality of first time periods.

Step S132: determining the minimum first mean heart-rate parameter as the first static heart-rate parameter.

For example, the first time interval includes five first time periods, which are first time period a, first time period b, first time period c, first time period d, and first time period e respectively. Correspondingly, a first mean heart-rate parameter corresponding to the first time period a is 80 beats/minute, a first mean heart-rate parameter corresponding to the first time period b is 85 beats/minute, a first mean heart-rate parameter corresponding to the first time period c is 90 beats/minute, a first mean heart-rate parameter corresponding to the first time period d is 75 beats/minute, and a first mean heart-rate parameter corresponding to the first time period e is 95 beats/minute. Then, the minimum first mean heart-rate parameter is the first mean heart-rate parameter corresponding to the first time period d (75 beats/minute). Therefore, as described in Step S132, the first mean heart-rate parameter corresponding to the first time period d (75 beats/minute) may be determined as the first static heart-rate parameter.

According to the embodiment of the present disclosure, by determining the minimum first mean heart-rate parameter among first mean heart-rate parameters respectively corresponding to a plurality of first time periods, and determining the minimum first mean heart-rate parameter as the first static heart-rate parameter, a purpose of determining, based on the first mean heart-rate parameters respectively corresponding to the plurality of first time periods, the first static heart-rate parameter is realized. As the minimum first mean heart-rate parameter among the first mean heart-rate parameters respectively corresponding to the plurality of first time periods may characterize a heart-rate characteristic of the subject to be tested in the first time interval to a certain extent, accuracy and comparability of first state information may be improved in the embodiment of the present disclosure.

FIG. 10 is a schematic flowchart of a method for determining, based on a preset analysis time interval, a state evaluation parameter corresponding to a subject to be tested according to another exemplary embodiment of the present disclosure. The embodiment shown in FIG. 10 is an extension of the embodiment shown in FIG. 8. Differences between the embodiment shown in FIG. 10 and the embodiment shown in FIG. 8 will be introduced below, and similarities will not be described herein again.

As shown in FIG. 10, in the state information determination method according to the embodiment of the present disclosure, after the step of determining, based on the first mean heart-rate parameters respectively corresponding to the plurality of first time periods, the first static heart-rate parameter, the method further includes the following steps.

Step S140: determining a first time period corresponding to the first static heart-rate parameter as a first static time period.

Step S150: determining a heart-rate variability parameter corresponding to the first static time period as the first static heart-rate variability parameter.

According to an embodiment of the present disclosure, the first static heart-rate variability parameter refers to a sleep rest heart rate variability (Sleep RHRV) parameter.

As the first static heart-rate variability parameter is determined based on the first static heart-rate parameter, an ability and comparability of characterizing state information (such as a neurohormone level and/or state) of a subject to be tested during the first time interval may be improved compared with the prior arts.

It should be noted that in another embodiment of the present disclosure, the first static heart-rate variability parameter may also be determined first, and then the first static heart-rate parameter is determined (this also applies to the second static heart-rate variability parameter and the second static heart-rate parameter, in other words, the second static heart-rate variability parameter may be determined first, and then the second static heart-rate parameter is determined). For example, based on the plurality of first time periods, first heart-rate variability parameters respectively corresponding to the first time periods are determined; based on the first heart-rate variability parameters respectively corresponding to the plurality of first time periods, a first static heart-rate variability parameter is determined; a first time period corresponding to the first static heart-rate variability parameter is determined as a first static time period; and a mean heart-rate parameter corresponding to the first static time period is determined as the first static heart-rate parameter. The step of determining, based on the first heart-rate variability parameters respectively corresponding to the plurality of first time periods, the first static heart-rate variability parameter may be executed as determining, based on a maximum first heart-rate variability parameter in the first heart-rate variability parameters respectively corresponding to the plurality of first time periods, the first static heart-rate variability parameter. Other statistical descriptions besides a maximum value may also be used here for heart-rate variability parameters, such as a 75% value. In addition, it should be noted that the mean heart-rate parameters may also be described in other statistical methods, such as a 25% value.

FIG. 11 is a schematic flowchart of a method for determining, based on a preset analysis time interval, a state evaluation parameter corresponding to a subject to be tested according to still another exemplary embodiment of the present disclosure. The embodiment shown in FIG. 11 is an extension of the embodiment shown in FIG. 3. Differences between the embodiment shown in FIG. 11 and the embodiment shown in FIG. 3 will be introduced below, and similarities will not be described herein again.

As shown in FIG. 11, in the state information determination method according to the embodiment of the present disclosure, the state evaluation parameter includes a second heart-rate characterization parameter, and the second heart-rate characterization parameter includes a second mean heart-rate parameter and a second static heart-rate parameter. And the step of determining, based on a preset analysis time interval, a state evaluation parameter corresponding to a subject to be tested includes the following steps.

Step S160: determining a plurality of second time periods, corresponding to the second time interval, of the preset analysis time interval.

Exemplarily, a second time period is a time window with a time length of 60 seconds.

Step S170: determining, based on the plurality of second time periods, second mean heart-rate parameters respectively corresponding to the plurality of second time periods.

In other words, step S160 and step S170 refer to determining, based on a plurality of time windows included in the second time interval, the second mean heart-rate parameters respectively corresponding to the plurality of time windows.

Optionally, the second mean heart-rate (MHR) parameter corresponding to each of the plurality of time windows refers to a mean heart rate measured during a corresponding time window Step S180: determining, based on the second mean heart-rate parameters respectively corresponding to the plurality of second time periods, the second static heart-rate parameter.

According to an embodiment of the present disclosure, the second static heart-rate parameter refers to a day rest heart rate (Day RHR) parameter.

As the second static heart-rate parameter is determined based on the second mean heart-rate parameters respectively corresponding to the plurality of second time periods, the second static heart-rate parameter obtained may fully consider characteristics of the second mean heart-rate parameters respectively corresponding to the plurality of the second time periods. Thus, the second static heart-rate parameter obtained may better characterize the heart rate situation of the subject to be tested in the second time interval.

Compared with a real-time heart rate, the second mean heart-rate parameters and the second static heart-rate parameter may more accurately characterize the heart rate condition of the subject to be tested in the second time interval. Thus, when state information of the subject to be tested in the second time interval (such as a neurohormone level and/or state information) is determined based on the second mean heart-rate parameters and the second static heart rate parameter obtained according to the embodiment of the present disclosure, a more accurate result may be obtained.

Another embodiment of the present disclosure is extended on the basis of the embodiment shown in FIG. 11. In the embodiment of the present disclosure, before the step of determining, based on a plurality of second time periods, second mean heart-rate parameters respectively corresponding to the plurality of second time periods, the method further includes: removing an unstable time interval corresponding to each of the plurality of second time periods. The step of determining, based on a plurality of second time periods, second mean heart-rate parameters respectively corresponding to the plurality of second time periods includes: determining, based on a plurality of second time periods without the unstable time interval, the second mean heart-rate parameters respectively corresponding to the plurality of second time periods.

Another embodiment of the present disclosure is extended on the basis of the embodiment shown in FIG. 11. In the embodiment of the present disclosure, the step of determining, based on second mean heart-rate parameters respectively corresponding to a plurality of second time periods, the second static heart-rate parameter includes: determining a minimum second mean heart-rate parameter among second mean heart-rate parameters respectively corresponding to a plurality of second time periods; and determining the minimum second mean heart-rate parameter as the second static heart-rate parameter. Other statistical descriptions may also used for the second static heart-rate parameter, such as a 25% value.

For example, the second time interval includes 3 second time periods, which are second time period a, second time period b, second time period c respectively. Correspondingly, a second mean heart-rate parameter corresponding to the second time period a is 80 beats/minute, a second mean heart-rate parameter corresponding to the second time period b is 85 beats/minute, and a second mean heart-rate parameter corresponding to the second time period c is 90 beats/minute. Then, the minimum second mean heart-rate parameter is the second mean heart-rate parameter corresponding to the second time period a (80 beats/minute). Therefore, the second mean heart-rate parameter corresponding to the second time period a (80 beats/minute) may be determined as the second static heart-rate parameter.

For the same reason, as the minimum second mean heart-rate parameter in the second mean heart-rate parameters respectively corresponding to the plurality of second time periods may characterize, to some extent, a heart-rate characteristic of the subject to be tested during the second time interval, the embodiment of the present disclosure may further enrich effective information contained in the state evaluation parameter. When a neurohormone level and/or state information of a subject to be tested is determined based on the state evaluation parameter, the embodiment of the present disclosure may further improve prediction accuracy and comparability of the neurohormone level and/or the state information.

FIG. 12 is a schematic flowchart of a method of determining, based on a preset analysis time interval, a state evaluation parameter corresponding to a subject to be tested according to yet another exemplary embodiment of the present disclosure. The embodiment shown in FIG. 12 is an extension of the embodiment shown in FIG. 11. Differences between the embodiment shown in FIG. 12 and the embodiment shown in FIG. 11 will be introduced below, and similarities will not be described herein again.

As shown in FIG. 12, in the state information determination method according to the embodiment of the present disclosure, after the step of determining, based on the second mean heart-rate parameters respectively corresponding to the plurality of second time periods, the second static heart-rate parameter, the method further includes the following steps.

Step S191: determining a second time period corresponding to the second static heart-rate parameter as a third static time period.

Step S192: determining a heart-rate variability parameter corresponding to the third static time period as the second static heart-rate variability parameter.

According to an embodiment of the present disclosure, the second static heart-rate variability parameter refers to a day rest heart rate variability (Day RHRV) parameter.

As the second static heart-rate variability parameter is determined based on the second static heart-rate parameter, an ability of characterizing state information (such as a neurohormone level and/or state information) of a subject to be tested during the second time interval by the second static heart-rate variability parameter may be improved compared with the prior arts.

FIG. 13 is a schematic flowchart of a control method according to an exemplary embodiment of the present disclosure. As shown in FIG. 13, the control method according to the embodiment of the present disclosure includes the following steps.

Step S300: obtaining first state information corresponding to a subject to be tested.

Exemplarily, the first state information mentioned in step S300 is obtained based on the state information determination method described in any one of the above embodiments.

Step S400: controlling, based on the first state information, a working state of a medical system and/or a medical device and/or a mobile device.

Exemplarily, the medical system mentioned in step S400 refers to a medical system that may be loaded in a medical device.

Exemplarily, the working state of the medical device includes a state of using a warning light source of different colors (such as yellow and/or red) for a warning purpose. It should be noted that the warning purpose of the medical device may alternatively be achieved without a help of the warning light source, but by means of vibration, sound, or a combination thereof.

For example, the first state information is absolute trend variation information. When the absolute trend variation information is always in a rising state within a preset time period, then a yellow warning light source of the medical device may be controlled to be turned on, in order to achieve a warning effect. Optionally, when the yellow warning light source is continuously turned on twice, a red warning light source of the medical device may be controlled to be turned on, in order to play a key warning effect.

In another embodiment of the present disclosure, the controlling a working state of a medical device includes controlling an on-off state of the medical device, and controlling an on-off state of other devices in communication connection with the medical device.

In an embodiment of the present disclosure, the mobile device includes, but is not limited to, a mobile phone, a tablet computer, and the like, of a patient or a family member of the patient, a doctor, or a nurse. Exemplarily, the controlling a working state of a mobile device based on first state information includes, but is not limited to, controlling, based on the first state information, an emergency information notification state of the mobile device, and the like, so that a patient and related personnel thereof may know a condition of the patient in time.

In practical applications, firstly, the first state information corresponding to a subject to be tested is obtained, and then the working state of the medical system and/or the medical device is controlled based on the first state information.

According to the control method provided by the embodiment of the present disclosure, by controlling, based on first state information, a working state of a medical system and/or a medical device, a purpose of timely and effectively informing and/or early warning, based on the state information corresponding to the subject to be tested, a state condition corresponding to the subject to be tested is realized.

Exemplary Device

FIG. 14 is a schematic structural diagram of a state information determination device according to an exemplary embodiment of the present disclosure. As shown in FIG. 14, a state information determination device according to the embodiment of the present disclosure includes:

a first determination module 100, configured to determine, based on a preset analysis time interval, a state evaluation parameter corresponding to a subject to be tested; and a second determination module 200, configured to determine, based on the state evaluation parameter, first state information corresponding to the subject to be tested.

FIG. 15 is a schematic structural diagram of a second determination module according to an exemplary embodiment of the present disclosure. The embodiment shown in FIG. 15 is an extension of the embodiment shown in FIG. 14. Differences between the embodiment shown in FIG. 15 and the embodiment shown in FIG. 14 will be introduced below, and similarities will not be described herein again.

As shown in FIG. 15, in the state information determination device according to the embodiment of the present disclosure, the second determination module 200 includes:

a numerical variation information determination unit 210, configured to determine, based on the state evaluation parameter, numerical variation information corresponding to the subject to be tested; and a first state information determination unit 220, configured to determine, based on the numerical variation information, the first state information.

FIG. 16 is a schematic structural diagram of a state information determination device according to another exemplary embodiment of the present disclosure. The embodiment shown in FIG. 16 is an extension of the embodiment shown in FIG. 14. Differences between the embodiment shown in FIG. 16 and the embodiment shown in FIG. 14 will be introduced below, and similarities will not be described herein again.

As shown in FIG. 16, the state information determination device according to the embodiment of the present disclosure further includes:

a second state information determination module 105, configured to determine, based on the state evaluation parameter, second state information corresponding to the subject to be tested.

In addition, in the embodiment of the present disclosure, a second determination module 200 includes:

a determination unit 230, configured to determine, based on the state evaluation parameter and the second state information, the first state information.

In an embodiment of the present disclosure, the determination unit 230 is also configured to compare the state evaluation parameter with second state information, so as to obtain a comparison result, and determine, based on the comparison result, the first state information.

FIG. 17 is a schematic structural diagram of a second state information determination module according to an exemplary embodiment of the present disclosure. The embodiment shown in FIG. 17 is an extension of the embodiment shown in FIG. 16. Differences between the embodiment shown in FIG. 17 and the embodiment shown in FIG. 11 will be introduced below, and similarities will not be described herein again.

As shown in FIG. 17, in the state information determination device according to the embodiment of the present disclosure, the second state information determination module 150 includes:

a state evaluation level determination unit 151, configured to determine, based on the state evaluation parameter, state evaluation levels respectively corresponding to the plurality of preset analysis time periods;

a level determination unit 152, configured to determine a lowest level or a baseline level (value) that meets a normal state level condition among the state evaluation levels respectively corresponding to the plurality of preset analysis time periods; and a second state information determination unit 153, configured to take state information of a preset analysis time period corresponding to the lowest level or the baseline level as the second state information.

FIG. 18 is a schematic structural diagram of a first determination module according to an exemplary embodiment of the present disclosure. The embodiment shown in FIG. 18 is an extension of the embodiment shown in FIG. 14. Differences between the embodiment shown in FIG. 18 and the embodiment shown in FIG. 14 will be introduced below, and similarities will not be described herein again.

As shown in FIG. 18, in the state information determination device according to the embodiment of the present disclosure, the first determination module 100 includes:

a first time period determination unit 110, configured to determine a plurality of first time periods, corresponding to a first time interval, of the preset analysis time interval;

a first mean heart-rate parameter determination unit 120, configured to determine, based on the plurality of first time periods, first mean heart-rate parameters respectively corresponding to the plurality of first time periods; and a first static heart-rate parameter determination unit 130, configured to determine, based on the first mean heart-rate parameters respectively corresponding to the plurality of first time periods, the first static heart-rate parameter.

In an embodiment of the present disclosure, the first static heart-rate parameter determination unit 130 is also configured to determine a minimum first mean heart-rate parameter among the first mean heart-rate parameters respectively corresponding to a plurality of first time periods, and determine the minimum first mean heart-rate parameter as the first static heart-rate parameter.

FIG. 19 is a schematic structural diagram of a first determination module according to another exemplary embodiment of the present disclosure. The embodiment shown in FIG. 19 is an extension of the embodiment shown in FIG. 18. Differences between the embodiment shown in FIG. 19 and the embodiment shown in FIG. 18 will be introduced below, and similarities will not be described herein again.

As shown in FIG. 19, in the state information determination device according to the embodiment of the present disclosure, the first determination module 100 further includes:

a first static time period determination unit 140, configured to determine a first time period corresponding to the first static heart-rate parameter as a first static time period; and a first static heart-rate variability parameter determination unit 150, configured to determine a heart-rate variability parameter corresponding to the first static time period as the first static heart-rate variability parameter.

FIG. 20 is a schematic structural diagram of a first determination module according to still another exemplary embodiment of the present disclosure. The embodiment shown in FIG. 20 is an extension of the embodiment shown in FIG. 14. Differences between the embodiment shown in FIG. 20 and the embodiment shown in FIG. 14 will be introduced below, and similarities will not be described herein again.

As shown in FIG. 20, in the state information determination device according to the embodiment of the present disclosure, the first determination module 100 includes:

a second time period determination unit 160, configured to determine a plurality of second time periods, corresponding to the second time interval, of the preset analysis time interval;

a second mean heart-rate parameter determination unit 170, configured to determine, based on the plurality of second time periods, second mean heart-rate parameters respectively corresponding to the plurality of second time periods; and a second static heart-rate parameter determination unit 180, configured to determine, based on the second mean heart-rate parameters respectively corresponding to the plurality of second time periods, the second static heart-rate parameter.

FIG. 21 is a schematic structural diagram of a first determination module according to yet another exemplary embodiment of the present disclosure. The embodiment shown in FIG. 21 is an extension of the embodiment shown in FIG. 20. Differences between the embodiment shown in FIG. 21 and the embodiment shown in FIG. 20 will be introduced below, and similarities will not be described herein again.

As shown in FIG. 21, in the state information determination device according to the embodiment of the present disclosure, the first determination module 100 further includes:

a third static time period determination unit 191, configured to determine a second time period corresponding to the second static heart-rate parameter as a third static time period; and a second static heart-rate variability parameter determination unit 192, configured to determine a heart-rate variability parameter corresponding to the third static time period as the second static heart-rate variability parameter.

Figure 22:
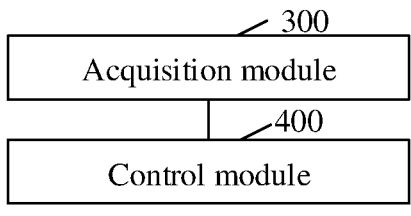
FIG. 22 is a schematic structural diagram of a control device according to an exemplary embodiment of the present disclosure.

FIG. 22 is a schematic structural diagram of a control device according to an exemplary embodiment of the present disclosure. As shown in FIG. 22, the control device provided in the embodiment of the present disclosure includes:

an acquisition module 300, configured to obtain first state information corresponding to a subject to be tested;

a control module 400, configured to control, based on the first state information, a working state of a medical system and/or a medical device.

It should be understood that, according to the state information determination device in FIG. 14 to FIG. 21, operations and functions of the first determination module 100, the second state information determination module 105 and the second determination module 200, and the first time period determination unit 110, the first mean heart-rate parameter determination unit 120, the first static heart-rate parameter determination unit 130, the first static time period determination unit 140, the first static heart-rate variability parameter determination unit 150, the second time period determination unit 160, the second mean heart-rate parameter determination unit 170, the second static heart-rate parameter determination unit 180, the third static time period determination unit 191 and the second static heart-rate variability parameter determination unit 192 included in the first determination module 100, and the state evaluating level determination unit 151, the level determination unit 152 and the second state information determination unit 153 included in the second state information determination module 150, and the numerical variation information determination unit 210, the first state information determination unit 220 and the determination unit 230 included in the second determination module 200 may be referred to the state information determination methods according to FIG. 3 to FIG. 12, and in order to avoid repetition, details are not described herein again.

In addition, it should be understood that, according to the control device in FIG. 22, an operation and a function of the obtaining module 300 and the control module 400 may be referred to the control method according to FIG. 13, and in order to avoid repetition, details are not described herein again.

Figure 23:
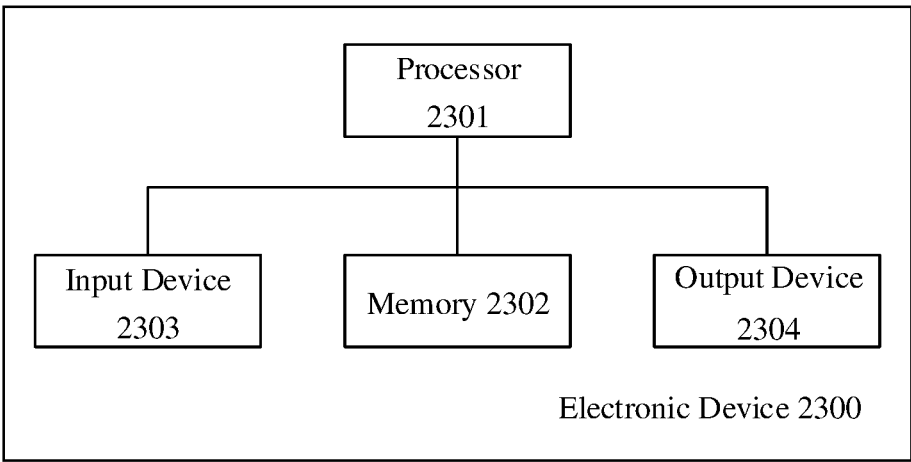
FIG. 23 is a schematic structural diagram of an electronic device according to an exemplary embodiment of the present disclosure.

Hereinafter, an electronic device according to an embodiment of the present disclosure is described with reference to FIG. 23. FIG. 23 is a schematic structural diagram of an electronic device according to an exemplary embodiment of the present disclosure.

As shown in FIG. 23, the electronic device 2300 includes: one or more processors 2301 and a memory 2302.

The processor 2301 may be a central processing unit (CPU) or other form of processing unit with data transmission capability and/or instruction execution capability, and may control other components in the electronic device 2300 to perform a desired function.

The memory 2302 may include one or more computer program products, which may include various forms of computer-readable storage media, such as volatile memory and/or non-volatile memory. The volatile memory may include, for example, random access memory (RAM) and/or cache memory (Cache). The non-volatile memory may include, for example, read only memory (ROM), hard disk, flash memory and so on. One or more computer program instructions may be stored in a computer-readable storage medium, and the processor 2301 may run the program instructions to realize the state information determination method, control method and/or other desired functions according to the embodiments of the present disclosure. And the computer-readable storage medium may further store various contents such as state evaluation information.

In an embodiment, the electronic device 2300 may further include an input device 2303 and an output device 2304. These components are interconnected by a bus system and/or other forms of connection mechanism (not shown).

The input device 2303 may include, for example, a keyboard, a mouse, and the like.

The output device 2304 may output various kinds of information, including first state information determined, to the outside. The output device 2304 may include, for example, a display, a speaker, a printer, a communication network and remote output device (such as a short message, a WeChat, an audio, a video, a mail, a mobile phone) connected on it, and so on.

To simplify, only some of the components related to the present disclosure in the electronic device 2300 are shown in FIG. 23 and components such as bus, input/output interface and so on are omitted. Moreover, the electronic device 2300 may also include any other appropriate components according to the specific disclosure.

Beyond the above methods and devices, the embodiments of the present disclosure may also be computer program products, including computer program instructions, which enable the processor to perform the steps of the state information determination method and the control method as described in any one of above embodiments when run by the processor.

The computer program product may write program code for executing the operation of the embodiments of the present disclosure in any combination of one or more programming languages. The programming languages include object-oriented programming languages, such as Java, C++, and also include conventional procedural programming languages, such as "C" language or similar programming languages. The program code may be completely executed on the user's computing device, partially executed on the user's device, executed as an independent software package, partially executed on the user's computing device and partially executed on the remote computing device, or completely executed on the remote computing device or processor.

Moreover, the embodiments of the present disclosure may also be a computer-readable storage medium on which computer executable instructions are stored. When the computer executable instructions are run by the processor, the processor performs the steps of the state information determination method and the control method described in the "exemplary method" according to the embodiments of the present disclosure.

The computer-readable storage medium may adopt any combination of one or more readable media. The readable medium may be a readable signal medium or a readable storage medium. The readable storage medium may include, for example, but not limited to, systems, apparatus or means of electricity, magnetism, light, electromagnetism, infrared ray, or semiconductor, or any combination of the above. More specific examples of readable storage media (not an exhaustive list) include: electronic connection with one or more wires, portable disk, hard disk, RAM, ROM, erasable programmable read only memory (EPROM) or flash memory, optical fiber, compact disk read only memory (CD-ROM), optical storage means, magnetic storage means, or any suitable combination of the above.

The above describes the basic principle of the present disclosure with reference to specific embodiments. However, it should be noted that the advantages, superiorities, effects and so on mentioned in the present disclosure are only examples, but not limitations. It cannot be considered that these advantages, superiorities, effects and so on are necessary for each embodiment of the present disclosure. In addition, the specific details disclosed above are only for the purpose of example and easy understanding, but not for limitation. The present disclosure is not limited to the above specific details.

The block diagrams of means, apparatus, devices and systems involved in the present disclosure are only illustrative examples and are not intended to require or imply that they must be connected, disposed and configured in the manner shown in the block diagram. As those skilled in the art will recognize, these means, apparatus, devices and systems can be connected, disposed and configured in any way. The terms such as "include", "contain", "have" and so on are open-class words, and referring to "include but not limited to", and can be used interchangeably. The terms "or" and "and" refer to the terms "and/or" and can be used interchangeably, unless the context clearly indicate otherwise. The term "such as" refers to the terms "such as but not limited to" and can be used interchangeably.

It should also be noted that each component or step in the apparatus, device and method of the present disclosure can be decomposed and/or reassembled. The decomposition and/or recombination shall be considered as the equivalent of the present disclosure.

The above description of the disclosed aspects is provided to enable any person skilled in the art to make or use the present disclosure. Any modification to these aspects is obvious to a person skilled in the art, and the general principles defined herein can be applied to other aspects without departing from the protection scope of the present disclosure. Therefore, the present disclosure is not intended to be limited to the aspects shown herein, but to the widest range consistent with the principles and novel features disclosed herein.

The above description has been given for the purpose of illustration and description. In addition, the description is not intended to limit the embodiments of the present disclosure to the form disclosed herein. Although several example aspects and embodiments have been discussed above, a person skilled in the art may recognize certain variations, modifications, changes, additions and sub-combinations thereof.

What is claimed is:

1. A state information determination method, comprising:
determining, based on a preset analysis time interval, a state evaluation parameter corresponding to a subject to be tested, wherein the state evaluation parameter comprises a first heart-rate characterization parameter, and the first heart-rate characterization parameter corresponds to a first time interval; and
determining, based on the state evaluation parameter, first state information corresponding to the subject to be tested;
wherein the first heart-rate characterization parameter comprises a first mean heart-rate parameter and a first static heart-rate parameter, and the determining, based on the preset analysis time interval, the state evaluation parameter corresponding to the subject to be tested comprises:
determining a plurality of first time periods, corresponding to the first time interval, of the preset analysis time interval;
determining, based on the plurality of first time periods, first mean heart-rate parameters respectively corresponding to the plurality of first time periods;
determining a minimum first mean heart-rate parameter among the first mean heart-rate parameters respectively corresponding to the plurality of first time periods; and
determining the minimum first mean heart-rate parameter as the first static heart-rate parameter.

2. The state information determination method according to claim 1, wherein before the determining, based on the state evaluation parameter, the first state information corresponding to the subject to be tested, the method further comprises:
determining, based on the state evaluation parameter, second state information corresponding to the subject to be tested;
wherein the determining, based on the state evaluation parameter, first state information corresponding to the subject to be tested comprises:
determining, based on the state evaluation parameter and the second state information, the first state information;
wherein the preset analysis time interval comprises a plurality of preset analysis time periods, and the determining, based on the state evaluation parameter, the second state information corresponding to the subject to be tested comprises:
determining, based on the state evaluation parameter, state evaluation levels respectively corresponding to the plurality of preset analysis time periods;
determining a lowest level or a baseline level among the state evaluation levels respectively corresponding to the plurality of preset analysis time periods that meet a normal state level condition; and
taking state information of a preset analysis time period corresponding to the lowest level or the baseline level as the second state information.

3. The state information determination method according to claim 2, wherein the determining, based on the state evaluation parameter and the second state information, the first state information comprises:
comparing the state evaluation parameter and the second state information to obtain a comparison result; and
determining, based on the comparison result, the first state information.

4. The state information determination method according to claim 1, wherein the state evaluation parameter further comprises a first heart-rate variability characterization parameter, the first heart-rate variability characterization parameter comprises a first static heart-rate variability parameter, and after the determining, based on the first mean heart-rate parameters respectively corresponding to the plurality of first time periods, the first static heart-rate parameter, the method further comprises:
determining a first time period corresponding to the first static heart-rate parameter as a first static time period; and
determining a heart-rate variability parameter corresponding to the first static time period as the first static heart-rate variability parameter.

5. The state information determination method according to claim 4, wherein the first static heart-rate variability parameter comprises a sleep rest heart-rate variability parameter, and the first static heart-rate parameter comprises a sleep rest heart-rate parameter.

6. The state information determination method according to claim 1, wherein before the determining, based on the plurality of first time periods, first mean heart-rate parameters respectively corresponding to the plurality of first time periods, the method further comprises:

removing an unstable time interval corresponding to each of the plurality of first time periods, wherein the determining, based on the plurality of first time periods, first mean heart-rate parameters respectively corresponding to the plurality of first time periods comprises:

determining, based on a plurality of first time periods without the unstable time interval, the first mean heart-rate parameters respectively corresponding to the plurality of first time periods.

7. The state information determination method according to claim 1, wherein the state evaluation parameter further comprises a second heart-rate characterization parameter and a second heart-rate variability characterization parameter, the second heart-rate characterization parameter comprises a second mean heart-rate parameter and a second static heart-rate parameter, the second heart-rate characterization parameter and the second heart-rate variability characterization parameter correspond to a second time interval; and the determining, based on a preset analysis time interval, a state evaluation parameter corresponding to a subject to be tested comprises:

determining a plurality of second time periods, corresponding to the second time interval, of the preset analysis time interval;

determining, based on the plurality of second time periods, second mean heart-rate parameters respectively corresponding to the plurality of second time periods;

determining, based on the second mean heart-rate parameters respectively corresponding to the plurality of second time periods, the second static heart-rate parameter;

determining a second time period corresponding to the second static heart-rate parameter as a third static time period; and determining a heart-rate variability parameter corresponding to the third static time period as the second static heart-rate variability parameter;

wherein the determining, based on the second mean heart-rate parameters respectively corresponding to the plurality of second time periods, the second static heart-rate parameter comprises:

determining a minimum second mean heart-rate parameter among the second mean heart-rate parameters respectively corresponding to the plurality of second time periods; and determining the minimum second mean heart-rate parameter as the second static heart-rate parameter.

8. The state information determination method according to claim 7, wherein before the determining, based on the plurality of second time periods, second mean heart-rate parameters respectively corresponding to the plurality of second time periods, the method further comprises:

removing an unstable time interval corresponding to each of the plurality of second time periods, wherein the determining, based on the plurality of second time periods, second mean heart-rate parameters respectively corresponding to the plurality of second time periods comprises:

determining, based on a plurality of second time periods without the unstable time interval, the second mean heart-rate parameters respectively corresponding to the plurality of second time periods.

9. The state information determination method according to claim 7, wherein the second static heart-rate variability parameter comprises a day rest heart-rate variability parameter, the second static heart-rate parameter comprises a day rest heart-rate parameter, the first time interval comprises a time interval from 22:00 of a current day to 6:00 of a next day, and the second time interval comprises a time interval from 8:00 to 20:00 of a current day.

10. A control method, comprising:

obtaining first state information corresponding to a subject to be tested, wherein the first state information is obtained based on the state information determination method according to claim 1; and controlling, based on the first state information, a working state of a medical system and/or a medical device and/or a mobile device.

11. A non-transitory computer-readable storage medium on which a computer program is stored, wherein the computer program is configured to perform the control method according to claim 10.

12. An electronic device, comprising:

a processor; and a memory, configured to store executable instructions of the processor, wherein the processor is configured to implement the control method according to claim 10.

13. A non-transitory computer-readable storage medium on which a computer program is stored, wherein the computer program is configured to perform the state information determination method according to claim 1.

14. An electronic device, comprising:

a processor; and a memory, configured to store executable instructions of the processor, wherein the processor is configured to implement the state information determination method according to claim 1.

15. A state information determination method, comprising:

determining, based on a preset analysis time interval, a state evaluation parameter corresponding to a subject to be tested, wherein the state evaluation parameter comprises a first heart-rate characterization parameter and a first heart-rate variability characterization parameter, the first heart-rate characterization parameter and the first heart-rate variability characterization parameter correspond to a first time interval; and determining, based on the state evaluation parameter, first state information corresponding to the subject to be tested;

wherein the first heart-rate characterization parameter comprises a first mean heart-rate parameter and a first static heart-rate parameter, the first heart-rate variability characterization parameter comprises a first static heart-rate variability parameter, and the determining, based on a preset analysis time interval, a state evaluation parameter corresponding to a subject to be tested comprises:

determining a plurality of first time periods, corresponding to the first time interval, of the preset analysis time interval;

determining, based on the plurality of first time periods, first mean heart-rate parameters respectively corresponding to the plurality of first time periods;

determining, based on the first mean heart-rate parameters respectively corresponding to the plurality of first time periods, the first static heart-rate parameter;

determining a first time period corresponding to the first static heart-rate parameter as a first static time period; and determining a heart-rate variability parameter corresponding to the first static time period as the first static heart-rate variability parameter.

16. A non-transitory computer-readable storage medium on which a computer program is stored, wherein the computer program is configured to perform the state information determination method according to claim 15.

17. A state information determination method, comprising:

determining, based on a preset analysis time interval, a state evaluation parameter corresponding to a subject to be tested, wherein the state evaluation parameter comprises a first heart-rate characterization parameter and a first heart-rate variability characterization parameter, the first heart-rate characterization parameter and the first heart-rate variability characterization parameter correspond to a first time interval; and determining, based on the state evaluation parameter, first state information corresponding to the subject to be tested;

wherein the first heart-rate characterization parameter comprises a first-mean heart-rate parameter and a first static heart-rate parameter, the first heart-rate variability characterization parameter comprises a first static heart-rate variability parameter, and the determining, based on a preset analysis time interval, a state evaluation parameter corresponding to a subject to be tested comprises:

determining a plurality of first time periods, corresponding to the first time interval, of the preset analysis time interval;

determining, based on the plurality of first time periods, first heart-rate variability parameters respectively corresponding to the first time periods;

determining, based on the first heart-rate variability parameters respectively corresponding to the plurality of first time periods, a first static heart-rate variability parameter;

determining a first time period corresponding to the first static heart-rate variability parameter as a first static time period; and determining the mean heart-rate parameter corresponding to the first static time period as the first static heart-rate parameter.

18. The state information determination method according to claim 17, wherein the determining, based on the first heart-rate variability parameters respectively corresponding to the plurality of first time periods, the first static heart-rate variability parameter comprises:

determining a maximum first heart-rate variability parameter in the first heart-rate variability parameters respectively corresponding to the plurality of first time periods; and determining the maximum first heart-rate variability parameter as the first static heart-rate variability parameter.

19. A non-transitory computer-readable storage medium on which a computer program is stored, wherein the computer program is configured to perform the state information determination method according to claim 17.

* * * * *